United States Patent [19]

Wei et al.

[11] Patent Number: 5,480,869
[45] Date of Patent: Jan. 2, 1996

[54] ANTI-INFLAMMATORY PEPTIDE ANALOGS AND TREATMENT TO INHIBIT VASCULAR LEAKAGE IN INJURED TISSUES

[75] Inventors: Edward T. Wei, Berkeley, Calif.; Holly A. Thomas, Wilmette, Ill.

[73] Assignee: The Regents of the University of California, Oakland, Calif.

[21] Appl. No.: 96,724

[22] Filed: Jul. 23, 1993

Related U.S. Application Data

[63] Continuation-in-part of Ser. No. 925,081, Aug. 4, 1992, abandoned, which is a continuation-in-part of Ser. No. 462,578, Jan. 9, 1990, Pat. No. 5,177,060.

[51] Int. Cl.$^6$ .............................. A61K 38/00; C07K 5/00; C07K 7/00; C07K 16/00
[52] U.S. Cl. .................. 514/16; 514/15; 514/14; 530/327; 530/328; 530/329
[58] Field of Search ..................................... 530/324, 326, 530/327, 328, 329; 514/12, 13, 14, 15, 16

[56] References Cited

U.S. PATENT DOCUMENTS

| | | | |
|---|---|---|---|
| 3,980,778 | 9/1976 | Ayer et al. | 514/171 |
| 4,091,090 | 5/1978 | Sipos | 424/45 |
| 4,404,198 | 9/1983 | Kelley | 514/159 |
| 4,415,558 | 11/1983 | Vale, Jr. et al. | 514/12 |
| 4,489,163 | 12/1984 | Rivier et al. | 436/86 |
| 4,528,189 | 7/1985 | Lederis et al. | 514/12 |
| 4,533,654 | 8/1985 | Lederis et al. | 514/12 |
| 4,579,844 | 4/1986 | Rovee et al. | 514/171 |
| 4,594,329 | 6/1986 | Vale, Jr. et al. | 514/12 |
| 4,801,612 | 1/1989 | Wei et al. | 514/12 |
| 4,883,863 | 11/1989 | Abe et al. | 530/331 |
| 4,895,931 | 1/1990 | Okazaki et al. | 530/326 |
| 4,923,963 | 5/1990 | Stewart et al. | 530/314 |
| 5,177,060 | 1/1993 | Wei | 514/15 |

FOREIGN PATENT DOCUMENTS

| 2193891 | 7/1990 | United Kingdom . |
|---|---|---|

OTHER PUBLICATIONS

Miele et al, *Nature*, vol. 335, 20 Oct. 1988, pp. 726–730.
Marki et al., *FEBS Letters*, vol. 264, No. 2, pp. 171–175, May 1990.
Pinckard et al., "Platelet–Activating Factors", pp. 139–167, Ch. 10 in *Inflammation: Basic Principles and Clinical Correlates*, eds. Gallin et al., New York: Raven Press (1988).
Persson, "The Role of Microvascular Permeability in Pathogenesis of Asthma", *European Journal of Respiratory Diseases*, Supp. No. 144, vol. 68 (1986), pp. 190–204.
Stern et al., "Ibuprofen in the Treatment of UV-B-Induced Inflammation", *Archives of Dermatology*, vol. 121, No. 4 (Apr. 1985), pp. 508–512.
Melchiorri et al., "Action of Sauvagine on the Mesenteric Vascular Bed of the Dog", *Regulatory Peptides*, vol. 2, (1981), pp. 1–13.
Ling et al., "Isolation and Characterization of Caprine Corticotropin-Releasing Factor", *Biochemical and Biophysical Research Communications*, vol. 122, No. 3 (1984), pp. 1218–1224.
Esch et al., "Isolation and Characterization of the Bovine Hypothalamic Corticotropin–Releasing Factor", *Biochemical and Biophysical Research Communications*, vol. 122, No. 3 (1984), pp. 899–905.
Patthy et al., "Isolation and Amino Acid Sequence of Corticotropin–Releasing Factor From Pig Hypothalami", *Proceedings of the National Academy of Sciences* vol. 82, No. 24 (Dec. 1985), pp. 8762–8766.
Montecucchi et al., "Amino Acid Composition and Sequence Analysis of Sauvagine, A New Active Peptide From the Skin of *Phyllomedusa Sauvagei*", *Int. Journal of Peptide and Protein Research*, vol. 18 (1981), pp. 113–120.
Montecucchi et al., "Secondary Structure Prediction of Sauvagine, a Novel Biologically Active Polypeptide From a Frog", *Int. Journal of Peptide and Protein Research*, vol. 20 (1982), pp. 139–143.
Pallai et al., "Structure Homology of Corticotropin–Releasing Factor, Sauvagine, and Urotensin I: Circular Dichroism and Prediction Studies", *Proc. Natl. Acad. Sci. USA*, vol. 80 (Nov. 1983), pp. 6770–6774.
Lau et al., "Surface Properties of an Amphiphilic Peptide Hormone and of its Analog: Corticotropin–Releasing Factor and Sauvagine", *Proc. Natl. Acad. Sci. USA*, vol. 80 (Dec. 1983), pp. 7070–7074.
Miele et al., "Novel Anti–Inflammatory Peptides From The Region of Highest Similarity Between Uteroglobin and Lipocortin I", *Nature*, vol. 335, (Oct. 1988), pp. 726–730.
van Binsbergen et al., "Synthetic Peptide From Lipocortin I Has No Phospholipase $A_2$ Inhibitory Activity", *FEB*, vol. 247, No. 2 (Apr. 1989), pp. 293–297.
Vostal t al., "Novel Peptides Derived From A Region of Local Homology Between Uteroglobin & Lipocortin–1 Inhibit Platelet Aggregation & Secretion", *Biochem. & Biophys. Res. Comm.*, vol. 165, No. 1 (Nov. 1989), pp. 27–36.
Hoekfelt et al., Abstract from *Chemical Abstracts*, vol. 108, No. 25 (1988) p. 180219h [of "Analysis of Peptide Histidine–Isoleucine/Vasoactive Intestinal Polypeptide . . . ", *Neuroscience*, vol. 108, No. 25, (1987)].

(List continued on next page.)

*Primary Examiner*—Jill Warden
*Assistant Examiner*—A. M. Davenport
*Attorney, Agent, or Firm*—Majestic, Parsons, Siebert & Hsue

[57] ABSTRACT

Small, anti-inflammatory compounds that are peptide analogs are described useful to inhibit inflammation of a mammal's skin, mucous membranes, or lacerations of the musculature or injury to the brain or leakage of fluids into the air spaces of the lungs. Peptide analogs of the invention have the primary sequence $T_N$-$A_1$-$A_2$-$A_3$-$A_4$-$A_5$-$A_6$-$T_C$ where one of the moieties is in the D-configuration. $A_1$ and $A_2$ are each a basic polar amino acids while each of $A_3$, $A_4$, and $A_6$ is a hydrophobic amino acid. $A_5$ can be a variety of structures and appears to function to optimize the spatial relationship between the hydrophobic and the basic residues. $T_N$ is selected or modified to convey resistance against enzymatic degradation. $T_C$ is an amino group or an amidated amino acid, preferably hydrophobic.

14 Claims, No Drawings

OTHER PUBLICATIONS

Wei et al., Abstract from *Chemical Abstracts*, vol. 111, No. 25, p. 225416a of "Peptides of the Corticoliberin Superfamily Attenuate Thermal and Neurogenic Inflammation in Rat Pawskin", *Eur. J. Pharmacol.*, vol. 168, No. 1 (1989).

Rudinger, "Characteristics of the Amino Acids as Components of a Peptide Hormone Sequence," pp. 1–7 in Peptide Hormones, ed. Parsons, Baltimore: University Park Press (Jun. 1976)

Orth et al., "Effect of Synthetic Ovine Corticotropin–Releasing Factor", *J. Clin. Invest.*, vol. 71, (Mar. 1983), pp. 587–595.

Ross et al., "Ovine Corticotropin–Releasing Hormone Stimulation Test in Normal Children," *J. Clin. Endocrin. & Metab.*, vol. 62, No. 2, (1986), pp. 390–392.

Fulcrand et al., "2–Phenylethyl Ester and 2–Phenylethyl Amide Derivative Analogues of the C–Terminal Hepta– and Octapeptide of Cholecystokinin" Int. J. Peptide Protein Res., vol. 32, (1988), pp. 384–395.

Porter et al., "Synthesis, Resolution and Characterization of Ring Substituted Phenylalanines and Tryptophans", *Int. J. Peptide Protein Res.* vol. 30, (1987), pp. 13–21.

Lugrin et al., "Reduced Peptide Bond Pseudopeptide Analogues of Neurotensin," *European Journal of Pharmacology*, vol. 205 (1991), pp. 191–198.

Nestor, Jr. et al., "Synthesis of a Novel Class of Heteroaromatic Amino Acids and Their Use in the Preparation of Analogues of Luteinizing Hormone–Releasing Hormone", *J. Med. Chem.*, vol. 27, (1984) pp. 320–325.

Nestor, Jr. et al., "Potent, Long–Acting Luteinizing Hormone–Releasing Hormone Antagonists Containing New Synthetic Amino Acids: N,N'–Dialkyl–$_D$–Homoarginines" *J. Med. Chem.*, vol. 31, (1988), pp. 65–72.

"Peptides," *Chemical Abstracts*, 102 (1985), entry 204302j, p. 634.

ANTI-INFLAMMATORY PEPTIDE ANALOGS AND TREATMENT TO INHIBIT VASCULAR LEAKAGE IN INJURED TISSUES

This is a continuation-in-part of U.S. patent application Ser. No. 07/925,081, filed Aug. 4, 1992 and now abandoned, which was a continuation-in-part of U.S. patent application Ser. No. 07/462,578 filed Jan. 9, 1990, now U.S. Pat. No. 5,177,060, issued Jan. 5, 1993, both of common assignment herewith.

FIELD OF THE INVENTION

This invention generally relates to antiinflammatory agents and to uses in reducing inflammatory responses, such as edema in connection with brain, skin, mucous membranes and muscle injuries, and more particularly to the use of relatively small, synthetic peptide analogs that have the property of inhibiting vascular leakage.

BACKGROUND OF THE INVENTION

Inflammation is signaled by redness, swelling, heat and pain as a reaction of the body against injury or assault. A variety of chemicals have been implicated as chemical mediators of the inflammatory reaction, including histamine, kinins, prostaglandins, platelet-activating factors, leukotrienes, and, from nerve endings, substance P. Mediators of the acute inflammatory reaction Seem to play roles in one or more of increasing vascular permeability, attracting leukocytes, producing pain, local edema and necrosis.

A variety of physiologic responses occur from the biological events that constitute the inflammatory processes. For example, Pinckard et al. at Chapter 10 describe platelet-activating factors ("PAF") in the text *Inflammation: Basic Principles and Clinical Correlates* (Gallin et al., Eds., 1988). This family of structurally related compounds appears to promote a variety of physiologic actions that are directly or indirectly related to inflammatory reactions. The authors note that PAF has been implicated in the pathogenesis of human disease conditions such as septic shock and organ transplantation rejection.

Swelling is a characteristic inflammatory response of tissues to injury. Swelling is produced by leakage of water and solutes of the blood directly into the tissue matrix. The increased leakiness of blood vessels after injury may be due to direct damage of blood vessels or may occur after the release of substances such as histamine (inflammatory mediators) that open up gaps between endothelial cells that line the blood vessels. A mild degree of swelling (or edema) does not affect the functional integrity of injured tissues (except perhaps in the brain), but, in severe injuries, massive swelling distorts tissue architecture, impedes the delivery of oxygen to cells, and causes extensive fluid loss from the vascular compartment. Thus, a pharmacological agent capable of inhibiting the swelling process may have therapeutic value in the treatment of tissue injuries.

Inflammation is also involved in various chronic conditions, such as asthma, although it is not presently clear which inflammatory cells or which particular mediators are significantly involved in asthma. Persson, "The Role of Microvascular Permeability in, the Pathogenesis of Asthma", *European Journal of Respiratory Diseases*, Suppl. No. 144, Vol. 68, pp. 190–204 (1986), concludes that extravasated plasma protein is always present in the airway lumen of asthmatic subjects.

There are steroid and non-steroid anti-inflammatory drugs known to the art. U.S. Pat. No. 4,579,844, inventors Rovee et al., issued Apr. 1, 1986, discloses topically treating an inflammatory condition of the skin by use of the prostaglandin synthetase inhibitor concurrently with a corticosteroid. U.S. Pat. No. 4,404,198, inventor Kelley, issued Sep. 13, 1983, discloses the topical application of a composition including phenyl salicylate to treat inflammation. U.S. Pat. No. 3,980,778, inventors Ayer et al., issued Sep. 14, 1976, discloses asteroid for use in the topical, oral or parenteral treatment of skin and mucous membrane inflammations. Ibuprofen (a known anti-inflammatory agent) has been tested in connection with UV-B-induced inflammation, but was found to have limited usefulness in treating sunburn reaction and is only somewhat more effective than placebo for the relief of symptoms associated with UV-B-induced inflammation after high dose UV-B phototherapy for psoriasis. Stern et al., *Arch. Derm.*, 121, pp. 508–512 (1985).

U.S. Pat. No. 4,801,612, inventor Wei, issued Jan. 31, 1989, discloses the use of inhibiting an inflammatory response in the skin or mucous membranes of a patient by administering corticotropin-releasing factor or its analogs.

The first corticotropin-releasing factor (CRF, also called CRH or corticoliberin) to be characterized was a 41-residue peptide isolated from ovine hypothalami by Vale et al. (1981). Subsequently, the sequence of human-CRF was deduced from cDNA studies and shown to be identical to rat-CRF. More recently, caprine, bovine, porcine, and white sucker fish CRF have been characterized. The CRF of hoofed animals show considerable differences from that of man, but the pig and fish sequences differ from the human/rat sequence by only two out of forty-one residues.

For some unknown reason, peptides with homologous structures to mammalian CRF are found in cells of certain frog skins and in the urophysis of fish. In fact, the structure of sauvagine, the 40 amino acid peptide isolated from the skins of Phyllomedusa frogs, was reported several years before Vale's description of ovine-CRF. The structure of sucker fish urotensin I was reported just months after the description of ovine-CRF and resulted from an independent line of inquiry by Lederis's group in Canada. Although sauvagine and urotensin I release adrenocorticotropin from the pituitary, the functions of these peptides in the tree-frog (Phyllomedusa species that live in arid regions of South America) and in the sucker fish remain unknown. Recently, it has been shown that the sucker fish has its own hypothalamic CRF which is very close in structure to h/rCRF. Thus, the sucker fish would not require urotensin I for neuroendocrine regulation because it already has CRF in its hypothalamus.

Rat corticotropin-releasing factor (hereinafter "CRF") is described in U.S. Pat. No. 4,489,163, inventors Rivier et al., issued Dec. 18, 1984.

U.S. Pat. No. 4,415,558, inventors Vale, Jr. et al., issued Nov. 15, 1983, describes the synthesis of sheep CRF, analogs, and isolation of the oCRF from ovine hypothalamic extracts. The synthetic oCRF was found to lower blood pressure.

The generally similar peptide, sauvagine, was described in Regulatory Peptides 2, 1–13 (1981). Sauvagine is reported to have biological activity in lowering blood pressure in mammals and stimulating the secretion of ACTH and β-endorphin.

U.S. Pat. No. 4,528,189, inventors Lederis et al., issued Jul. 9, 1985, and U.S. Pat. No. 4,533,654, inventors Lederis et al., issued Aug. 6, 1985, describe white sucker and carp urotensin I, respectively, as stimulating ACTH and lowering blood pressure.

The other CRF-related peptide, white sucker fish urotensin I, has an amino acid sequence the same as the carp urotensin, except the amino acid at the 24 position is Isoleucine and the amino acid at the 27 position is Glutamic Acid.

Ling et al., *BBRC*, 122, pp. 1218–1224 (1984), disclose the structure of goat CRF, which is the same as that of sheep. Esch et al., *BBRC*, 122, pp. 899–905 (1984), disclose the structure of bovine CRF which differs from sheep and goat CRF only by one amino acid residue (number 33 which is asparagine rather than the number 33 serine of goat and sheep CRF). Porcine CRF has been isolated and characterized by Patthy et al., *Proc. Natl. Acad. Sci.*, 82, pp. 8762–8766 (1985). Porcine CRF shares a common amino acid sequence (residues 1–39) with rat/human CRF and differs from these only in position 40 and 41. Residue 40 can be either asparagine or isoleucine and residue 41 is phenylalanine-amide.

Both ovine and human/rat CRF have been used in clinical studies on the endocrine function of the pituitary-adrenal axis. Usually, doses of 1 to 5 μg/kg have been injected intravenously to elicit endogenous release of adrenocorticotropin and increases in plasma corticosteroids. Higher doses of 10 μg/kg and 30 μg/kg of ovine-CRF were used by Orth et al., "Effect of synthetic ovine corticotropin-releasing factor. Dose-response of plasma adrenocorticotropin and cortisol.", *J. Clin. Invest.*, 71, pp. 587–595 (1983), in the initial assessment of this hormone in man. The non-endocrine effects of this hormone include symptoms such as flushing, shortness of breath and physical signs such as an increase in minute volume, tachycardia and possible hypotension. These parameters return to baseline levels within 30 minutes and were not considered to be clinically harmful. The relative safety of CRF peptides is illustrated by the fact that CRF has been evaluated in normal children (aged 6–15 years) at a dose of 1 μg/kg administered as an intravenous bolus, as reported by J. L. Ross, et al., "Ovine corticotropin-releasing hormone stimulation test in normal children", *J. Clin. Endocrinol. Metab.*, 62, pp. 390–392 (1986).

Traditionally, pharmacologists have searched for new drugs that act as specific antagonists of inflammatory mediators. For example, candidate drugs that act as antagonists of the inflammatory mediators platelet-activating factor, leukotrienes, and bradykinin have been described. Specific mediator antagonists, by design, work one-on-one against substances that promote inflammation, and the efficacy of a single antagonist may be limited if more than one mediator is released during tissue injury. By contrast, an agonist, a term introduced by Reuse to describe a chemical that activates biological events, would be more efficacious than an antagonist if it could suppress convergent inflammatory processes initiated by more than one mediator. The concept of drugs as anti-inflammatory agonists was discussed by Svensjo and Persson in 1985 who showed that clinically used asthma drugs such as the β$_2$-adrenergic agonist terbutaline and the xanthine drug theophylline acted on specific receptors in the microvasculature to shut off plasma protein leakage induced by the inflammatory mediators histamine and bradykinin.

However, it would be advantageous to have peptides shorter than either CRF, sauvagine or urotensin I that possess anti-inflammatory agonist activity and that are efficacious for reducing vascular leakage. For example, the costs of producing a peptide with seven to twelve amino acid residues would be much less than the costs of producing one that is forty or forty-one residues long because each residue must be added to the next residue in a step-wise fashion. Also, the possibilities of obtaining more selective biological actions or oral/topical activity from shorter peptides are potential advantages to be considered.

SUMMARY OF THE INVENTION

It is an object of the present invention to provide relatively small, synthetic peptide analogs that can be used to inhibit inflammation of the skin, the mucous membranes and to decrease the leakage of blood components into the brain tissue, lung alveoli or air spaces of the lung, and musculature. Skin and mucous membrane inflammations can occur from thermal (extremes of heat or cold) or traumatic injury, or from noxious endogenous or exogenous substances. Leakage of blood components into the brain tissue, a condition called vasogenic edema of the brain, can be produced by various adverse medical conditions, such as brain ischemia, brain infarction, intracranial hemorrhage from neurosurgical operations, and so forth.

Compounds of the invention have a peptide or peptide derived backbone in which an amino terminal moiety is linked to a carboxyl terminal moiety by a moiety sometimes hereinafter described as "$A_5$", which is part of the backbone and which preferably is selected substantially to enhance a determinable anti-inflammatory property of the inventive analogs (such as in comparison, with respect to, peptides corresponding thereto but with $A_5$ being Glu, as are described in the related issued patent of which this is a continuation-in-part). The $A_5$ moiety is believed to function in establishing a spatial relationship between hydrophobic and basic portions of the inventive compounds.

In one aspect of the present invention, an anti-inflammatory peptide analog is provided having the primary sequence $T_N$-$A_1$-$A_2$-$A_3$-$A_4$-$A_5$-$A_6$-$T_C$ in which $T_N$ is an amino terminal portion having a molecular weight less than about 600 daltons, $A_1$ through $A_4$ and $A_6$ each is an amino acid (synthetic or natural), at least one of which is in the D-configuration, and together with $A_5$ constitute an active core effective in providing anti-inflammatory activity to the peptide, and $T_C$ is part of or comprises an amidated carboxyl terminal portion. Use of one or more D-amino acid residues can result in peptides that are several times more potent than a corresponding sequence containing only L-amino acid residues.

The $A_5$ can be a variety of moieties, with particularly preferred $A_5$ moieties including an anisolylated glutamic acid, a methoxy substituted tyrosine, a D-proline, D-thioproline, or β-thienyl-D-alanine.

$T_N$ is selected or modified to convey resistance against enzymatic degradation of the active core. Each of $A_1$ and $A_2$ is a basic polar amino acid in the D- or L- configuration. Each of $A_3$, $A_4$ and $A_6$ is a non-polar amino acid in the D- or L-configuration. $T_C$ is an amino group or an amidated amino acid, preferably an amidated hydrophobic amino acid.

Particularly preferred peptides of this invention are where $T_N$ is an amino terminal portion having a molecular weight less than about 600 daltons and is selected to convey resistance against enzymatic degradation, a preferred $T_N$, for example, being N-acetylated Tyr(Me) or para-methoxybenzoyl; $A_1$ is D- or L-arginine and D-lysine; $A_2$ is lysine or arginine; $A_3$ is leucine or isoleucine; $A_4$ is leucine, isoleucine, methionine, or valine; $A_5$ is para-methoxybenzoylethyl-Gly, para-methoxybenzoylmethyl-D-Ala, Tyr(Me), Trp, Tyr, Leu, Lys, Arg, 4' substituted Phe (4'F, 4'I, 4'Cl, 4'NO$_2$), D-His, D-Lys, D-Arg, D-Leu, D-Pro, or D-Trp; $A_6$ is isoleucine; with the proviso that not all of $A_1$–$A_6$ are in the L-configuration; and $T_C$ is isoleucineamide, D-leucineamide, D-valineamide.

The class of anti-inflammatory peptides having the above-described primary sequence, or structure, are sometimes hereinafter called "nocifensins" because they defend tissue against noxious stimuli and can be used as anti-inflammatory agents.

A therapeutically effective amount of an inventive nocifensin peptide can be administered, preferably by intravenous, intradermal or subcutaneous means, such as in doses from about 0.01 to 2 mg/kg. Such administrations reduce the permeability of brain and central nervous system blood vessels and are of therapeutic value in the treatment of tissue injury, such as brain and central nervous system injuries. Administrations also provide clinical benefits when used to limit or minimize leakage of blood constituent into tissue during surgery, to alleviate pain and discomfort, and to prevent further swelling for patients already experiencing inflammation.

DETAILED DESCRIPTION OF THE PREFERRED EMBODIMENT

When the brain is injured such as in brain ischemia, or infarction, then vasogenic edema occurs and the increased amounts of water compress and distort brain tissue architecture and impede the delivery of oxygen to brain cells. The patient can lose consciousness and stop breathing. When the skin or a mucosal surface is injured by extreme heat or cold, by trauma or assaulted by noxious substances, it is converted from a condition of balanced fluid exchange to a state in which serum and its solutes freely pass into the surrounding tissues. In general, substances are released, either from nerve endings or from cells within the injured tissue, that produce increased vascular permeability. Fluids and proteins in the blood then move from the vascular compartment to the tissue compartment with pain, swelling and tissue damage as a result.

In the present invention, a nocifensive peptide analog (or a salt form thereof) can be used to inhibit inflammation of a mammal's skin, mucous membranes, or where there have been (or will be) lacerations of the musculature or injury to the brain or leakage of fluids into the air spaces of the lung. Administration can include intravascular, oral or topical means at dosages of between about 0.01 to 5 mg/kg body weight. However, administration is preferably by intravenous, intradermal, or subcutaneous injection with at least a single dose being given, preferably from about 0.01 to 0.5 mg/kg body weight, and can be about two hours before deliberate lacerations of the musculature (such as during abdominal or orthopedic surgery) and can be up to one week after surgery or accidental injury. Administration is most preferably via the blood stream, but local application into the cerebrospinal fluid, brain, airways, or into the muscle can be used.

Because the nocifensive peptides have the property of inhibiting vascular leakage from tissues, they are useful in a number of different therapeutic applications. Specific tissues for which clinical usage of these peptides may be applied include skin and mucous membranes (eyelids, nasal membranes, oropharyngeal membranes, upper respiratory tract, esophagus, lower digestive tract), skeletal muscle, smooth muscle, cardiac muscle, blood vessels of the brain, and blood vessels of the lungs, liver, and kidneys. For example, therapeutic uses of these peptides include administration to treat thermal burns, irradiation burns, infection, or for other inflammatory conditions of the skin. The peptides may be used to reduce swelling, pain, and plasma extravasation. For irritants deposited on the upper airways or in chronic allergic conditions such as asthma, the peptides may be used to decrease irritancy, bronchial inflammation, edema and plasma extravasation. For lacerative or traumatic injuries to all tissues, such as might occur after knife wounds, surgical operations, and automobile accidents, the peptides may be used to reduce swelling, pain, and inflammation. For tissue infarcts, which result in tissue hypoxia, ischemic anoxia and edema, such as occur after brain strokes or myocardial infarcts, the peptides may be used to reduce passage of blood constituents into the tissue matrix and enhance survival of the remaining tissues. For preventing the actions of endogenous or exogenous chemicals that directly injure the endothelium, such as endotoxins or inflammatory mediators, resulting in the clinical condition of septic shock, the peptides may be useful in reducing the loss of blood volume. Administration may be used for preserving the integrity of the vascular tree of an organ prior to or during its removal for transplantation, such organs being kidneys, liver, or heart.

The nocifensive peptides may be administered in combination with a pharmaceutically acceptable carrier, such as isotonic saline, phosphate buffer solution or the like. Topical administration is also feasible since the peptides are relatively small.

Compositions and excipients useful for the administration of small peptides through the nasal mucosa are, for example, described by U.K. patent application No. 8719248, published Feb. 24, 1988, applicant Sandoz Limited. Topical compositions with enhanced penetration through intact skin preferably include a potentiator, many of which are described by U.S. Pat. No. 4,091,090, issued May 23, 1978, inventor Sipos. The nocifensive peptides form pharmaceutically acceptable salts with organic and inorganic acids and can be administered in salt form. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethane- and hydroxyethane- sulfonic.

Salts may also be formed with suitable organic pharmaceutically acceptable base addition salts. These organic bases form a class whose limits are readily understood by those skilled in the art. Merely for purposes of illustration, the class may be said to include mono., di-, and trialkyamines, such as methylamine, dimethylamine, and triethylamine; mono-, di-or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66 (1) pp. 1–19 (1977).

Nocifensive peptide analogs of the invention have the primary sequence $T_N$-$A_1$-$A_2$-$A_3$-$A_4$-$A_5$-$A_6$-$T_C$ where at least one of the amino acid residues or analogs is in the D-configuration. We will indicate the presence of a D amino acid residue configuration in particular sequences by the use of a lower case letter (for example, "l" to indicate D-leucine) where the letter used will follow the conventional one letter system. (By primary sequence, or structure, we mean a covalent backbone of a polypeptide chain or of a peptide derived chain and is used to denote the sequence of its amino acid residues or the amino acid residue analogs. By "peptide derived" we intend to include peptide analogs where peptide bonds have been replaced by derivatives, such as, for example, with $CH_2NH$, ($\Psi$ reduced) bonds. The approach of replacing the peptide bond with a reduced bond has been used in developing antagonists for gastrin, bombesin, substance P, and secretin, and for neurotensin analogs.) The amino terminal, or $T_N$, has a molecular weight less than about 600 daltons and is selected or modified to convey resistance against enzymatic degradation of the active core for the inventive peptide. Preferred moieties for $T_N$ are (degradation) protected amino acids or derivatives thereof. Particularly preferred for $T_N$ is N-acetylated Tyr(Me) or para-methoxybenzoyl. Derivatives suitable for $T_N$ are N-methylphenylalanine or pyroglutamic acid. Other examples of moieties useful to convey resistance against enzymatic degradation are p-chloro-or p-nitrophenylalanine, lower alkyl alkylated arginine and lysine, the o-ethyl ethers of asparagine and glutamine and para-methoxy benzoyl. The introduction of a pseudopeptide bond between the first and second amino acid residues of the N-terminus will also confer resistance to enzymatic degradation, as described by Lugrin et al., *Europ. J. Pharmacol.*, 205, pp. 191–198 (1991). Unnatural amino acids to stabilize or to increase potency and prolong duration of action are illustrated, for example by the articles of Nestor et al., *J. Medicinal Chem.*, 31 (1), pp. 65–72 (1988) and 27, pp. 320–325 (1984).

$A_1$ and $A_2$ are each a basic polar amino acid (synthetic or natural). $A_1$ and $A_2$ can be in the D- or L- configuration and each is preferably selected from arginine and lysine. We will sometimes hereinafter use the single letter code for amino acid residues with a capital letter signifying the L-amino acid residue and a lower case letter signifying the D-amino acid residue.

Each of $A_3$, $A_4$ and $A_6$ is a hydrophobic, or nonpolar, amino acid preferably selected from leucine, isoleucine, valine, and methionine.

In the now issued parent patent, $A_5$ was described as an acidic polar amino acid, preferably glutamic acid and aspartic acid. We have found that $A_5$ can be replaced with a number of other moieties, most (but not all) of which are modified amino acids, such as the anisolylated derivative of glutamyl residue, and yet obtain the result of anti-inflammatory activity, indeed to obtain enhanced activity. That is, $A_5$ is "promiscuous," and a variety of substitutions can be made in this position, yet the entire peptide molecule can bind to its receptor and elicit anti-inflammatory effects. Thus, we will describe a variety of structures that can be placed in the $A_5$ position so that the molecules still retain biological activity as small novel anti-inflammatory peptides. Indeed, many of the substitutions (and preferred substitutions) result in enhanced activity.

$A_1$ through $A_6$ together constitute an active core for the peptide that is effective in providing anti-inflammatory activity to the peptide. Since $A_1$ and $A_2$ are each a polar (basic) amino acid (in the D- or L-configuration), together they constitute a hydrophilic region for the secondary structure of the peptide. Since each of $A_3$, $A_4$, and $A_6$, is a non-polar amino acid (in the D- or L-configuration), together $A_3$, $A_4$, and $A_6$ constitute a hydrophobic region for the secondary structure of the peptide. When the active core is a mixture of D- and L- configurations, then they are believed to form a "random coil." Because polar residues will associate together, as will hydrophobic residues, the molecules have an amphiphilic character.

The imposition of local conformational constraints, such as by adding methyl groups to the $\alpha$-carbon, regional constraints, for example, by adding bulky groups to $A_5$, or structured constraints by cyclization, for example, by forming ring structures with the addition of disulfide bridges, are believed to enhance potency for the small peptide analogs of this invention by assisting in stabilizing conformations in biological solutions. Without being bound to a particular theory, we suggest that the intrinsic biological activity of the peptides, based on 3-dimensional structures during functioning of the peptides, is likely to have three to four of the hydrophobic residues ($A_3$, $A_4$, $A_6$, and the preferred $T_C$) gathered together to activate the receptor, the two basic groups ($A_1$ and $A_2$) binding to acidic sites on biological surface (for anchorage), and with the $A_5$ moiety optimizing the spatial relationship between the hydrophobic and the basic residues. In receptor terminology, the basic residues are likely the "address" to the receptor-and the hydrophobic residues likely activate the "message" to the anti-inflammatory receptor.

In the now issued patent of which this is a continuation-in-part, $A_5$ was described as preferably glutamic acid, asparagine, or glutamine, and peptides were illustrated where $A_5$ was glutamic acid, glutamine, aspartic acid, and D-glutamic acid. We have discovered that anisolylated derivatives can be 20 to 38 times more potent for the present invention than glutamic acid substituted peptides of the parent application.

We believe an anisolylated derivative was initially formed as a by-product of the temperature-dependent Friedel-Crafts acylation reaction which occurs during hydrogen fluoride cleavage of glutamyl-containing peptides. Instead of the free glutamic carboxylic acid group, anisole in the cleavage mixtures reacts with the hydroxyl group to form an anisolylated derivative.

$$\begin{array}{c} \text{OH} \\ | \\ \text{C}=\text{O} \\ | \\ \text{CH}_2 \\ | \\ \text{CH}_2 \\ | \\ \text{peptide-HN}-\text{CH}-\text{C}=\text{O} \\ | \\ \text{NH-peptide} \end{array} + \text{CH}_3\text{-}\phi \xrightarrow{\text{HF}}_{\text{RT}}$$

$$\begin{array}{c} \text{p-CH}_3\text{O}-\phi \\ | \\ \text{C}=\text{O} \\ | \\ \text{CH}_2 \\ | \\ \text{CH}_2 \\ | \\ \text{peptide-HN}-\text{CH}-\text{C}=\text{O} \\ | \\ \text{NH-peptide} \end{array}$$

Use of other moieties for $A_5$ (other than an anisolylated glutamic acid derivative) are contemplated and within the scope of the present invention. Thus, suitable modified amino acids or moieties for $A_5$ include standard ring-substituted Phe and Trp derivatives (see Porter et al., *Int. J. Peptide Protein Res.*, 30 (1987), pp. 13–21, incorporated herein by reference) and synthetic hydrophobic D-amino acids (Nestor et al., supra, 1984, 1988), These include mono-halogenated, di-halogenated, or nitrated Phe, O-methylated derivatives, and substituted naphthyl and indole compounds. Other moieties, not listed in the Porter et al. paper, are alkoxy substitutes (e.g. p-ethoxy instead of p-methoxy on the benzene ring). Also suitable are substituted (such as with halogen, nitro, or lower alkoxy) and non-substituted heterocyclic rings such as thienyl, pyridyl, nicotinyl, and thiazole derivatives; substituted and non-substituted aliphatic compounds, e.g., butyl and amyl derivatives; and combinations of the above, e.g. homotyrosine, with or without keto groups on the aliphatic radical. Several illustrative examples of $A_5$ moieties for peptide analogs of the invention with heterocyclic and non-heterocyclic rings are 3-(2-naphthyl)-D-alanine, 3-(3-pyridyl)-D-alanine, N-ε-nicotinoyl-D-lysine, 4-chloro-D-phenylalanine, and D-thioproline.

We also expect

derivatives to be generally active, where X=benzene. For example, Flucrand et al., *Int. J. Peptide Protein Res.*, 32, pp. 384–395 (1988), describe 2-phenylethyl derivatives in peptides, and these substituents on X could possess anti-inflammatory properties. For Gly-X, one would expect alkylation (e.g. methylation or ethylation) of the amino group on the alpha-carbon to enhance potency by conferring resistance to enzymatic degradation (see, for example, Hardy et al., *J. Med. Chem.*, 1988). Other standard p-Phe substituents are p-ethoxy substituents instead of p-methoxy on the benzene ring.

In addition to the $A_5$ variations, it is also believed possible to vary the other residues by substitution of either the second basic residue (that is, $A_2$) or the third hydrophobic residue ($A_6$) with D- or L- asparagine or glutamine or citrulline, although potency is a likely to be diminished.

Finally, $T_C$ is an amino group or an amidated amino acid, preferably hydrophobic. Particularly preferred amidated amino acids are D-leucineamide, isoleucineamide, and D-valineamide as resistant to enzymatic degradation from the C-terminus. A non-polar aromatic residue such as phenylalanine or tyrosine is also a suitable moiety for $T_C$.

Particularly preferred peptides of this invention are where at least one amino acid residue or analog is in the D-configuration and where $T_N$ is an amino terminal portion having a molecular weight less than about 600 daltons and is selected to convey resistance against enzymatic degradation; $A_1$ is D- or L-arginine and D-lysine; $A_2$ is lysine or arginine; $A_3$ is leucine or isoleucine; $A_4$ is leucine, isoleucine, methionine, or valine; $A_5$ is *, D-*, β-thienyl-D-Ala, Tyr(Me), Trp, Tyr, Leu, Lys, Arg, substituted Phe (4'F, 4'I, 4'Cl, 4'NO₂), D-His, D-Lys, D-Arg, D-Leu, D-Pro, D-Trp The nocifensin peptides can be synthesized by various suitable, chemical methods, preferably by solid phase synthesis, manual or automated, as first developed by R. B. Merrifield and described by J. M. Stewart and J. D. Young in "Solid Phase Peptide Synthesis" (1984), incorporated herein by reference. Where, for example, one uses solid phase synthesis and after the completely blocked peptide is assembled on the resin support, one varies the usual procedure when reagents are applied to cleave the peptide from the resin and to remove the side chain blocking groups. The usual procedure is that the final cleavage and deprotection of the protected peptide resin requires acidolysis with hydrogen fluoride (HF), the nucleophilic scavengers dimethylsulfide and anisole, and is traditionally done at 0° C. for 30 minutes. However, to obtain the unusual function, which we sometimes also call "anisolylated Glu" or para-methoxybenzoyl-ethyl-Gly, which is illustrated below:

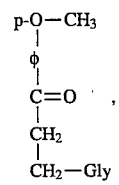

instead of Glu. When there is a D-configuration of this moiety (and since Gly by it self does not have stereoisomers), we shall use the terminology "para-methoxybenzoyl-methyl-D-Ala.

HF cleavage is conducted at room temperature for three hours in excess anisole. Removal of the HF under vacuum in the cleavage apparatus precedes multiple washes of the peptide-resin with dry ethyl ether and/or chloroform for extraction. Filtration follows with one molar aqueous acetic acid, with the obtained filtrate frozen and lyophilized. The used resin is weighed to determine the yield of peptide, and the need for any re-extraction. Finally, the synthesized peptides are purified by ion-exchange chromatography and by preparative HPLC. The purity of samples are verified by analytical HPLC and the structure of synthesized products are confirmed by analysis of amino acid composition and mass spectrometry.

A number of the inventive nocifensin peptides have been synthesized and tested by means of a bioassay for anti-inflammatory activity. Example 1 illustrates preparation of a particularly preferred peptide analog of this invention.

EXAMPLE 1

The synthesis of the preferred peptide analog of this invention having the formula

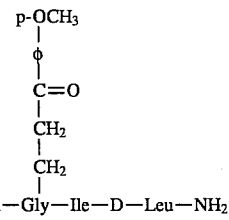

D—Ala—His—Ser—D—Asn—Arg—Lys—Leu—Met—Gly—Ile—D—Leu—NH₂

(where *=para-methoxybenzoylethyl-Gly and D-* is para-methoxybenzoylmethyl-D-Ala); $A_6$ is isoleucine; and $T_C$ is isoleucineamide, D-leucineamide, D-valineamide.

was conducted sequentially from the C-terminal amide end on a 4-methylbenzhydrylamine hydrochloride resin (MBHA HCl resin), as commercially available with amine substitution range of 0.4 to 0.6 millimoles per gram resin (CalBiochem, Inc., Bachem, Inc.). Normally the amount of resin equal to one millimole of active amine is washed with appropriate solvents (dichloromethane and/or methanol). Neutralization of the MBHA resin with triethylamine (TEA)in dichloromethane (DCM) removes the salt form, enabling sequential addition of the tertiarybutyloxycarbonyl (Boc) protected amino acid derivatives. The C-terminal residue, Boc-D-leucine (monohydrate), as coupled to the reactive resin amine groups with one molar dicyclohexycarbodiimide (DCC) in dichloromethane (DCM). Generally equimolar amounts of coupling agent (DCC) and Boc-amino acid are added in excess (five-fold) relative to the resin. The Boc-amino acids are dissolved in dichloromethane (DCM) and/or dimethylformamide (DMF) depending on the particular residue's solubility. After acidic deprotection with trifluoroacetic acid solution (25% in dichloromethane) and neutralization with triethylamine (10%) in dichloromethane, the stepwise building continues toward the amino end. Boc-arginine (Tos), Boc-histidine (Tos), and Boc-D-asparagine were coupled in a 9:1 mixture of dimethylformamide (DMF) and dichloromethane (DCM). P-toluenesulfonyl (Tos) groups are used to protect the guanidine of arginine and the imidazole of histidine. A xanthyl (Xan) ring is used to protect the amido group of asparagine. 2-Chlorobenzyloxycarbonyl (2-Clz) is used for the lysine side chain. The benzyl ether (Bzl) is used with the hydroxyl of serine, and the benzyl ester (OBzl) used for blocking the carboxyl of glutamic acid. Finishing the protected amino acid couplings, gives the following intermediates: Boc-D-Ala His(Tos) -Ser-(Bzl)-D-Asn(Xan)-Arg(Tos)-Lys(2Clz)-Leu-Met-Glu-(OBzl)-Ile-D-Leu-resin support.

EXAMPLE 2

In a similar manner to that described for the Example 1 peptide analog, but with other variations, peptide analogs were prepared in accordance with the invention having different moieties at the various $T_N$, $A_1$, $A_2$, $A_3$, $A_4$, $A_5$, $A_6$, and $T_C$ positions, as follows:

| Position | Variations |
| --- | --- |
| $T_N$ | H, Acetyl, |
|  | D—Ala—His—Ser—D—Asn—, |
|  | D—Leu—Ala—Thr—D—Tyr—, |
|  | Ala—His—Ser—Asn, |
|  | Acetyl-Tyr(Me), para-methoxybenzoyl |
| $A_1$ | Arg, D—Arg, D—Lys |
| $A_2$ | Lys, Arg |
| $A_3$ | Leu, Ile |
| $A_4$ | Ile, Met, Leu, Val |
| $A_5$ | *, D-*, Tyr-(4'Me), Trp, Tyr, Leu, Lys, Arg, substituted Phe(4'F, 4'I, 4'Cl, 4'NO$_2$), D—His, D—Lys, D—Arg, D—Leu, D—Pro, D—Trp (* = para-methoxy-benzoylethyl-Gly and D-* = para-methoxybenzoylmethyl-D—Ala), β-thienyl-D—Ala |
| $A_6$ | Ile |
| $T_C$ | Ile, D—Leu, D—Val amides |

Other peptide analogs of interest are Ac-Tyr(Me)RKLLχIl-NH$_2$ where χ is 3-(2-naphthyl)-D-alanine, 3-(3-pyridyl)-D-alanine, N-ε-nicotinoyl-D-lysine, 4-chloro-D-phenylalanine, D-thioproline, and β-thienyl-D-alanine.

As already noted, the anisolylated derivatives were 20 to 38 times more potent that glutamic acid substituted peptides. The D-amino acid substituted aHSnRKLM*Il-NH$_2$ was about three times more potent than an analogous sequence containing only L-amino acids. Replacement of Met with Leu in position 8 yielded undecapeptides with increased activities, the most potent being 1ATyRKLL*Il-NH$_2$. Because the anisole derivative of Glu is a para-methoxybenzene group, we substituted Tyr(Me) for Glu in position 9 of the 11-mer. The peptide aHSnRKLMY(Me)Il-NH$_2$ had excellent anti-inflammatory potency. Further, aHSnRKLM*Il-NH$_2$ and 1ATyRKLL*Il-NH$_2$ were tested in the epinephrine-induced pulmonary edema model and shown to have ED50 of 40 µg/kg i.v.

EXAMPLE 3

The inventive peptides were dissolved either in saline or saline acidified with 0.1 M acetic acid and injected intravenously into a pentobarbital-anesthetized rat. The rat's hind paw was then immersed in 58°–60° C. water for 1 minute and the increase in paw weight, as an index of edema and swelling, was measured 30 minutes later. For some peptides, the ability of the substances to inhibit vascular leakage after muscle injury was also tested. Normally, the paw weight of saline-treated animals (controls) will increase by about 65–95% after heat injury. The increase in weight is relative to the contralateral non-heated paw.

In screening the bioactivity of new peptides, a dose of 5 mg/kg i.v. was initially used. In later studies, when greater activity was expected, a screening dose of 1 to 2 mg/kg i.v. was used. For peptides that exhibited particularly significant activity, a full dose-response analysis was conducted according to the method of Litchfield and Wilcoxon.

Thus, each peptide was injected intravenously (at the amounts specified, usually 1 or 5 mg/kg, or by full dose-response analysis) 10 minutes (for 7/8-mers) or one hour (for 11-mers) before immersion of the right paw in 58° C. water, for 1 minute, and weights of both paws were obtained 30minutes later. To obtain statistical accuracy, four to six animals were used in each group. The % wt increase was calculated as (wt of heated paw—wt of unheated paw/wt of unheated paw)×100 and converted to % of the saline control group values, which were run concurrently. The weight of the-paws of the saline-treated animals did not increase after immersion in room temperature (22° C.) water, but increased by 65 to 95% after heat.

Eight of the 11-mer inventive peptides have dose-response data summarized below by Table 1.

TABLE 1

| Inventive Peptide | $ED_{50}$ (95% confidence limits) mg/kg i.v. |
| --- | --- |
| 1ATyRKLL(β-thienyl-D—Ala)Il-NH$_2$ | 0.015 (0.006–0.036) |
| 1ATyRKLL*Il-NH$_2$ | 0.05 (0.02–0.12) |
| aHSnRKLL*Il-NH$_2$ | 0.11 (0.04–0.29) |
| aHSnRKLMY(Me)Il-NH$_2$ | 0.16 (0.10–0.26) |
| aHSnRKLM*Il-NH$_2$ | 0.24 (0.09–0.60) |
| AHSNRKLM*Il-NH$_2$ | 0.88 (0.52–1.49) |
| 1ATyRKLLEIl-NH$_2$ | 1.9 (1.1–3.8) |
| aHSnRKLLEIl-NH$_2$ | 2.2 (1.4–3.6) |

We conclude from our work with the 11-mer inventive peptides that: (1) substitution of E with the anisolylated derivative (*) or β-thienyl-D-Ala increased potency, and (2) a heptapeptide sequence was particularly important for activity, this sequence being either -RKLMxIl-NH$_2$ or -RKLLxIl-NH$_2$, where x=*, Tyr(Me) or other derivatives for $A_5$ such as have been suggested.

EXAMPLE 4

We synthesized and tested 7-mer peptides of the invention where substitutions were made in the fifth residue. The most potent 7-mers in this series were those containing the anisolylated Glu residue (*) (particularly as the D-amino acid derivative) and para-chloro-phenylalanine. Table 2 compares four control peptides (where $A_5$ was proline, histidine, alanine, phenylalanine, respectively) with fourteen inventive peptides (where $A_5$ was tyrosine, leucine, tryptophan, lysine, arginine, D-proline, substituted phenylalanine (where the substituents were at the four prime position and were three different halogen and a nitro, respectively), an anisolylated amino acid residue, and methoxy substituted tyrosine, respectively).

TABLE 2[a]

| Composition Number | | Dose mg/kg i.v. | Heat-Edema % Saline Values |
|---|---|---|---|
| | Control Peptides | | |
| 1c | R K L M P I l-NH₂ | 5 | 114 ± 5 N.S.[b] |
| 2c | R K L M H I l-NH₂ | 5 | 106 ± 6 N.S. |
| 3c | R K L L A I l-NH₂ | 5 | 100 ± 4 N.S. |
| 4c | R K L M F I l-NH₂ | 5 | 93 ± 6 N.S. |
| | Inventive Peptides | | |
| 5 | R K L M Y I l-NH₂ | 5 | 70 ± 9[c] |
| 6 | R K L M L I l-NH₂ | 5 | 67 ± 10 |
| 7 | R K L M W I l-NH₂ | 5 | 38 ± 5 |
| 8 | R K L L K I l-NH₂ | 5 | 38 ± 10 |
| 9 | R K L L R I l-NH₂ | 5 | 18 ± 3 |
| 10 | R K L L F (4'F) I l-NH₂ | 5 | 54 ± 11 |
| 11 | R K L L F (4'I) I l-NH₂ | 5 | 49 ± 6 |
| 12 | R K L L F (4'NO₂) I l-NH₂ | 5 | 41 ± 6 |
| 13 | R K L L F (4'Cl) I l-NH₂ | 5 | 15 ± 5 |
| 14 | R K L M p I l-NH₂ | 2 | 21 ± 3 |
| 15 | R K L L (D-*) I l-NH₂ | 1 | 44 ± 13 |
| 16 | Ac-k K L M Y(Me) I l-NH₂ | 2 | 67 ± 11 |
| 17 | Ac-R K L V Y(Me) I l-NH₂ | 2 | 49 ± 9 |
| 18 | Ac-R K L M Y(Me) I l-NH₂ | 2 | 27 ± 1 |
| 19 | Ac-R K L L k I l-NH₂ | 1 | 23 ± 8 |

[a]Ten minute interval between peptide administration and exposure to 58° C. water for 1 minute, edema was measured 30 minutes after heat.
[b]N.S., not statistically different from saline control groups.
[c]All other tested peptides showed significant inhibition.

As can be seen from the data of Table 2, the four control peptides (designated composition numbers 1c, 2c, 3c, and 4c) provided substantially no anti-inflammatory activity when administered at 5 mg/kg i.v. ten minutes before the heat traumatic exposure. By contrast, inventive peptides (composition numbers 5—13) when administered in the same dose and procedure reduced inflammation with respect to the saline values significantly with inventive peptide number 13 (having a chlorine substituent at the 4' position of the phenylalanine ring) resulted in only 15% heat induced edema with respect to control. Further, inventive peptides (composition numbers 14–19) provided excellent anti-inflammatory results when administered at even lower doses.

It was discovered that bulky hydrophobic amino acid residues in the D-amino acid conformation at $A_5$ provided the best increase in potency. Thus, D-Trp, (anisolylated D-Glu, or "D-*"), D-Pro, β-thienyl-D-Ala, D-Leu, D-Lys, D-Arg, and D-His substituted 7-mers all significantly inhibited edema formation after heat, relative to saline-injected controls.

Table 3 shows the dose-responses of these inventive peptides.

TABLE 3[a]

| Composition Number | Inventive Peptide | ED⁵⁰ (95% confidence limits) mg/kg i.v. |
|---|---|---|
| 20 | R K L L h I l - NH₂ | 2.3 (1.2–4.2) |
| 21 | R K L L r I l -NH₂ | 2.0 (0.80–5.0) |
| 22 | R K L M * I l -NH₂ | 1.6 (0.70–3.6) |
| 23 | R K L L l I l -NH₂ | 1.3 (0.50–3.6) |
| 24 | R K L L w I l -NH₂ | 0.82 (0.56–1.2) |
| 25 | Ac-R K L M Y(Me) I v -NH₂ | 1.0 (0.52–1.9) |
| 26 | Ac-R R I I Y(Me) I l -NH₂ | 0.70 (0.40–1.2) |
| 27 | Ac-r K L M Y(Me) I l -NH₂ | 0.52 (0.19-1.8) |
| 28 | Ac-R K L M * I l -NH₂ | 0.46 (0.24–0.89) |
| 29 | Ac-Y(Me) R K L M Y(Me) I l-NH₂ | 0.22 (0.09–0.55) |
| 30 | 4-methoxybenzoyl-R K L L (β-thienyl-D—Ala) Il-NH₂) | 0.034 (0.023–0.050) |

[a]Ten minute interval between peptide administration and exposure to 58° C. water for 1 minute, with edema being measured 30 minutes after heat exposure As shown by Table 3 inventive peptides (composition numbers 20–24) provided median effective dosages from between about 2.3 mg/kg to about 0.82 mg/kg. Compositions 5–15 and 20–24 were designed to mimic physiological situations where the peptide is not protected on the N-terminus by a synthetic substituent. These peptides were administered at a relatively high dose to study activity of the $A_5$ substituent. Although the term "7-mer" is sometimes used herein, the "core" of the molecule is believed to be six amino acids.

Noteworthy is a comparison between peptide composition number 22 and peptide composition number 28. These two peptides differed only by composition number 28 having a N-acetylation to increase resistance to enzymatic degradation, which substantially increased potency as shown by comparing the median effective dosages of the two peptides. Even more striking is the yet further increased potency of inventive peptide composition number 29 where the addition of a methoxy substituted tyrosine (at the $T_N$ moiety) result in an increased potency. Finally, protection of the $T_N$ with a para-methoxybenzoyl moiety, combined with β-thienyl-D-Ala group as $A_5$ resulted in a peptide (no. 30) with potent biological activity.

Although the tested 7-mers (with the exception of number 30) appear to be less potent than the 11-mers, they shed light on the central core of the molecule that is critical for anti-inflammatory activity. It is likely that the active "core" for anti-inflammatory activity consists of no more than six residues with the addition of a D-leucineamide at carboxyl terminus ($T_C$) to confer resistance against enzymatic degradation. In accord with the parent application of which this is a continuation in part, the structural characteristics for activity are: the first two residues are basic (Arg or Lys), the second two residues are hydrophobic (Met, Leu, Ile, Val), and the sixth residue is hydrophobic with $T_C$ also preferably being hydrophobic (Ile, Leu, Met, Val).

N-Acetylation of the amino terminus of peptides is a standard procedure for enhancing potency because the N-acetylated peptide is less susceptible to the actions of aminopeptidase in tissues that degrade peptides. N-Acetylated 7-mers with Tyr(Me) at $A_5$ were synthesized. Tables 2 and 3 summarize the data.

(1) Valine substitution for Leu or Met in $A_4$ (Composition 17) retains activity, albeit at a lower potency. Similarly, D-valine (Composition 25) instead of D-leucine at $T_C$ retains activity. We believe this interchangeability is because Leu, Met., Ile, and Val are grouped together as amino acids with common hydrophobic and lipophilic physical chemical properties.

(2) In position $A_1$, D-Lys (Composition 16) can substitute for Arg and the basic residues Arg or Lys can be in the D-conformation with retention of activity. In position $A_2$ (Composition 26), Arg can replace Lys to yield potent anti-inflammatory properties. These results are believed due to Arg and Lys being grouped together as basic residues.

(3) In position $T_N$, addition of AcTyr(Me) or para-methoxybenzoyl enhanced potency of the 7-mer, as might be expected of a moiety that increases resistance to degradation.

In sum, the inventive nocifensins should find use in treating injured and inflamed tissues such as involved in trauma (brain tissue), burn injury (skin tissue), asthma (mucosa), and surgery (abdominal and/or orthopedic muscles).

It is to be understood that while the invention has been described above in conjunction with preferred specific embodiments, the description and examples are intended to illustrate and not limit the scope of the invention, which is defined by the scope of the appended claims.

It is claimed:

1. An anti-inflammatory peptide analog, having the structure $T_n$-$A_1$-$A_2$-$A_3$-$A_4$-$A_5$-$A_6$-$T_c$ wherein at least one moiety of the structure has a D-configuration, $T_n$ is an amino terminal portion having a molecular weight less than about 600 daltons and is selected to convey resistance against enzymatic degradation, $T_c$ is D- or L- leucineamide, isoleucineamide, or D-valineamide, $A_1$ is D- or L- arginine or lysine, $A_2$ is D- or L- arginine or lysine, $A_3$ is D- or L- isoleucine, leucine, methionine, or valine, $A_4$ is D- or L- isoleucine, leucine, methionine, or valine, $A_5$ is D- or L-anisolylated glutamine or glutamic acid, a D- or L-anisolylated glutamine or glutamic acid derivative, para-methoxybenzoylethyl-Gly, para-methoxybenzoylmethyl-D-Ala, Tyr(Me), Trp, Tyr, Leu, Lys, Arg, 4' substituted Phe (where the substituent is 4'F, 4'I, 4'Cl, or 4'NO$_2$), D-His, D-Lys, D-Arg, D-Leu, D-Pro, D-Trp, or β-thienyl D-Ala, and $A_6$ is D- or L- isoleucine, leucine, methionine, or valine.

2. The peptide analog as in claim 1 wherein $T_N$ is di-, tri-, tetra-, or pentapeptide or a derivative thereof, or is para-methoxy benzoyl.

3. The peptide analog as in claim 1 wherein:

$T_N$ includes D-asparagine, D-tyrosine, or D-glutamine adjacent to the amino acid at $A_1$.

4. The peptide analog as in claim 2 wherein:

the derivative of $T_N$ includes N-methylphenylalanine, pyroglutamic acid, or N-acetyl-tyrosine (4'Me).

5. The peptide analog as in claim 1 wherein $A_5$ is a D- or L- anisolylated amino acid or D- or L- anisolylated amino acid derivative.

6. A compound having the structure $T_n$-$A_1$-$A_2$-$A_3$-$A_4$-$A_5$-$A_6$-$T_c$ where $A_5$ is para-methoxybenzoylethyl-Gly, para-methoxybenzoylmethyl-D-Ala, Tyr(Me), Trp, Tyr, Leu, Lys, Arg, 4' substituted Phe (where the substituent is 4'F, 4'I, 4'Cl, or 4'NO2), D-His, D-Lys, D-A g, D-Leu, D-Pro, D-Trp, β-thienyl-D-Ala, or D-thioproline and wherein $T_n$ of the amino terminal moiety has a molecular weight less than about 600 daltons and is selected to convey resistance against enzymatic degradation, each of $A_1$ and $A_2$ is a basic amino acid in the D- or L- configuration, each of $A_3$, $A_4$, and $A_6$ is a hydrophobic amino acid in the D- or L-configuration, and $T_c$ of the carboxyl terminal moiety is isoleucineamide, leucineamide, or valineamide, all in either the L- or D- configuration, and at least one moiety of the structure is an amino acid residue or analog in the D-configuration.

7. The compound as in claims 6 wherein $A_1$ is arginine or lysine, $A_2$ is arginine or lysine, $A_3$ is leucine, isoleucine, or methionine, $A_4$ is leucine, isoleucine, methionine, or valine, and $A_6$ is leucine, isoleucine, or methionine.

8. An anti-inflammatory composition comprising:

a peptide analog in an amount effective to reduce inflammation, the peptide analog with at least one amino acid residue or analog in the D-configuration and having the structure $T_n$-$A_1$-$A_2$-$A_3$-$A_4$-$A_5$-$A_6$-$T_c$ wherein at least one moiety of the structure has a D-configuration, $T_n$ is an amino terminal portion having a molecular weight less than about 600 daltons and is selected to convey resistance against enzymatic degradation, $T_c$ is D- or L-leucineamide, isoleucineamide, or D-valineamide, $A_1$ is D- or L- arginine or lysine, $A_2$ is D- or L- arginine or lysine, $A_3$ is D- or L- methionine, leucine, or isoleucine, $A_4$ is D- or L- isoleucine, leucine, methionine, or valine, $A_6$ is D- or L- isoleucine, leucine, methionine, or valine and, $A_5$ is a D- or L- amino acid or D- or L- amino acid derivative excluding L-aspartic acid, L-glutamic acid and L-glutamine; and, a pharmaceutically acceptable carrier.

9. The composition as in claim 8 wherein the peptide analog is in a concentration sufficient to provide about 0.01 mg/kg body weight to about 2 mg/kg body weight when administered by intravenous, intradermal, or subcutaneous injection.

10. A method for treating a patient for an inflammatory condition, comprising:

administering a therapeutically effective amount of an anti-inflammatory peptide analog, effective to alleviate the symptoms of inflammatory response, the peptide analog having the structure $T_n$-$A_1$-$A_2$-$A_3$-$A_4$-$A_5$-$A_6$-$T_c$ wherein at least one moiety of the structure has a D-configuration, $T_n$ is an amino terminal portion having a molecular weight less than about 600 daltons and is selected to convey resistance against enzymatic degradation, $T_c$ is D- or L-leucineamide, isoleucineamide, or D-valineamide, $A_1$ is D- or L-arginine or lysine $A_2$ is D- or L-arginine or lysine, $A_3$ is D- or L-isoleucine, leucine, methionine, or valine, $A_4$ is D- or L-isoleucine, leucine, methionine, or valine, $A_6$ is D- or L-isoleucine, leucine, methionine, or valine and, $A_5$ is a D- or L-amino acid or D- or L-amino acid derivative except L-aspartic acid, L-glutamic acid and L-glutamine.

11. The method as in claim 10 wherein the administering is intravenous, intradermal, or subcutaneous.

12. A method for treating a patient with tissue injury, comprising:

administering a therapeutically effective amount of an anti-inflammatory peptide analog, effective to alleviate the symptoms of inflammatory response, the peptide analog having the structure $$T_n\text{-}A_1\text{-}A_2\text{-}A_3\text{-}A_4\text{-}A_5\text{-}A_6\text{-}T_c$$

wherein at least one moiety of the structure has a D-configuration, $T_n$ is an amino terminal portion having a molecular weight less than about 600 daltons and is selected to convex resistance against enzymatic degradation, $T_c$ is D- or L-leucineamide, isoleucineamide, or D-valineamide, $A_1$ is D- or L-arginine or lysine, $A_2$ is D- or L-arginine or lysine, $A_3$ is D- or L-isoleucine, leucine, methionine, or valine, $A_4$ is D- or L-isoleucine, leucine, methionine, or valine, $A_6$ is D- or L-isoleucine, leucine, methionine, or valine and, $A_5$ is a D- or L-amino acid or D- or L-amino acid derivative except L-aspartic acid, L-glutamic acid and L-glutamine.

13. The method as in claim 11 wherein the administering is intravenous, intradermal, or subcutaneous.

14. The method as in claim 11 wherein the amount administered is from about 0.01 mg/kg to about 2 mg/kg of patient body weight.

* * * * *

UNITED STATES PATENT AND TRADEMARK OFFICE
CERTIFICATE OF CORRECTION

PATENT NO.   :   5,480,869
DATED        :   January 2, 1996
INVENTOR(S)  :   Edward T. Wei
                 Holly A. Thomas It is certified that error appears in the above-indentified patent and that said Letters Patent is hereby corrected as shown below:

In Column 16, line 4 in Claim 6:
    replace "4'NO2), D-His, D-Lys, D-A g, D-Leu, D-Pro, D-Trp, β-thie-"
    with:

--4'NO2), D-His, D-Lys, D-Arg, D-Leu, D-Pro, D-Trp, β-thie---

Signed and Sealed this

Sixteenth Day of September, 1997

Attest:

BRUCE LEHMAN

*Attesting Officer*      *Commissioner of Patents and Trademarks*